(12) United States Patent
Yang et al.

(10) Patent No.: US 9,022,937 B2
(45) Date of Patent: May 5, 2015

(54) ULTRASOUND DEVICE AND METHOD FOR REAL-TIME COMPUTATION OF POINT-BY-POINT APODIZATION COEFFICIENTS WITH TRIGONOMETRIC FUNCTIONS

(75) Inventors: Bo Yang, Shenzhen (CN); Pengfei Yang, Shenzhen (CN); Qinjun Hu, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 2133 days.

(21) Appl. No.: 11/967,866

(22) Filed: Dec. 31, 2007

(65) Prior Publication Data
US 2009/0054780 A1    Feb. 26, 2009

(30) Foreign Application Priority Data
Aug. 24, 2007    (CN) .......................... 2007 1 0141485

(51) Int. Cl.
| | | |
|---|---|---|
| A61B 8/00 | (2006.01) | |
| G03B 42/06 | (2006.01) | |
| G10K 11/34 | (2006.01) | |

(52) U.S. Cl.
CPC . *G03B 42/06* (2013.01); *A61B 8/00* (2013.01); *G10K 11/346* (2013.01)

(58) Field of Classification Search
CPC ....... A61B 8/00; G10K 11/346; G10K 11/341
USPC .................. 73/602, 606, 626, 632, 633, 641; 600/437, 443, 447, 454, 455, 458, 472; 382/107, 336; 367/7; 345/427
See application file for complete search history.

(56) References Cited

U.S. PATENT DOCUMENTS

| | | | | |
|---|---|---|---|---|
| 4,030,343 A | * | 6/1977 | Lund et al. ...................... | 73/626 |
| 4,145,680 A | * | 3/1979 | Smith .............................. | 367/7 |
| 4,694,434 A | * | 9/1987 | von Ramm et al. .............. | 367/7 |
| 5,019,968 A | * | 5/1991 | Wang et al. ...................... | 712/4 |
| 5,485,842 A | * | 1/1996 | Quistgaard .................. | 600/443 |
| 5,522,393 A | * | 6/1996 | Phillips et al. ................ | 600/455 |

(Continued)

FOREIGN PATENT DOCUMENTS

| | | |
|---|---|---|
| CN | 1190753 C | 8/1998 |
| CN | 100337595 C | 3/2005 |
| CN | 20061006969.5 | 8/2006 |

*Primary Examiner* — Unsu Jung
*Assistant Examiner* — Serkan Akar
(74) *Attorney, Agent, or Firm* — Kory D. Christensen; Stoel Rives LLP

(57) ABSTRACT

A method for real-time computation of point-by-point apodization coefficients used for beam-forming includes storing apodization coefficients of receiving focus points in memory, and computing at least one of an included angle between a vector from a transducer element to a receiving point and a normal vector of the transducer element, and a trigonometric function value of the included angle. The method also includes addressing the memory storing the apodization coefficients according to the quantized included angle or trigonometric function value, and reading the apodization coefficients. In one embodiment, the method may include computing in advance apodization coefficients of a receiving focus point as the starting point for the subsequent interpolation operation and another receiving focus point as the ending point, and deriving, for each receiving channel, apodization coefficients of the points situated between these two receiving focus points through an interpolation operation.

18 Claims, 8 Drawing Sheets

(56) References Cited

U.S. PATENT DOCUMENTS

| | | | |
|---|---|---|---|
| 5,544,128 A | 8/1996 | Kim et al. | |
| 5,546,807 A * | 8/1996 | Oxaal et al. | 73/606 |
| 5,573,001 A * | 11/1996 | Petrofsky et al. | 600/447 |
| 5,600,581 A * | 2/1997 | Dworkin et al. | 708/277 |
| 5,676,147 A * | 10/1997 | Petrofsky et al. | 600/447 |
| 5,677,491 A * | 10/1997 | Ishrak et al. | 73/641 |
| 5,684,937 A * | 11/1997 | Oxaal | 345/427 |
| 5,901,708 A * | 5/1999 | Chang et al. | 600/443 |
| 5,922,962 A * | 7/1999 | Ishrak et al. | 73/632 |
| 5,936,630 A * | 8/1999 | Oxaal | 345/427 |
| 6,029,116 A * | 2/2000 | Wright et al. | 702/32 |
| 6,123,671 A * | 9/2000 | Miller | 600/447 |
| 6,126,600 A * | 10/2000 | Oxaal et al. | 600/439 |
| 6,159,153 A * | 12/2000 | Dubberstein et al. | 600/443 |
| 6,179,780 B1 * | 1/2001 | Hossack et al. | 600/437 |
| 6,231,511 B1 * | 5/2001 | Bae | 600/447 |
| 6,241,675 B1 * | 6/2001 | Smith et al. | 600/443 |
| 6,252,975 B1 * | 6/2001 | Bozdagi et al. | 382/107 |
| 6,276,211 B1 * | 8/2001 | Smith | 73/626 |
| 6,305,225 B1 * | 10/2001 | Bae et al. | 73/602 |
| 6,374,674 B1 * | 4/2002 | Mine | 73/606 |
| 6,537,219 B2 * | 3/2003 | Poland et al. | 600/447 |
| 6,589,179 B2 * | 7/2003 | Criton et al. | 600/454 |
| 6,622,562 B2 * | 9/2003 | Angelsen et al. | 73/633 |
| 6,709,395 B2 * | 3/2004 | Poland | 600/447 |
| 6,918,876 B1 * | 7/2005 | Kamiyama | 600/447 |
| 7,635,332 B2 * | 12/2009 | Ladabaum et al. | 600/437 |
| 7,713,208 B2 * | 5/2010 | Kamiyama | 600/458 |
| 7,800,979 B2 * | 9/2010 | Hu et al. | 367/138 |
| 7,850,611 B2 * | 12/2010 | Davies et al. | 600/447 |
| 2001/0051772 A1 * | 12/2001 | Bae | 600/447 |
| 2002/0120196 A1 * | 8/2002 | Dubberstein et al. | 600/447 |
| 2005/0033168 A1 * | 2/2005 | Shifrin | 600/437 |
| 2007/0269071 A1 * | 11/2007 | Hooley | 381/336 |
| 2008/0033299 A1 * | 2/2008 | Hu et al. | 600/472 |
| 2009/0054780 A1 * | 2/2009 | Yang et al. | 600/447 |

* cited by examiner

ULTRASOUND DEVICE AND METHOD FOR REAL-TIME COMPUTATION OF POINT-BY-POINT APODIZATION COEFFICIENTS WITH TRIGONOMETRIC FUNCTIONS

RELATED APPLICATIONS

The present application claims priority to Chinese Patent Application No. 200710141485.6, filed on Aug. 24, 2007, which is hereby incorporated by reference herein in its entirety.

TECHNICAL FIELD

The present disclosure relates to a method and device for computing apodization coefficients used for ultrasonic imaging.

SUMMARY

A method and device provide real-time computation of apodization coefficients used for ultrasonic beam-forming to achieve point-by-point apodization. The disclosed method realizes point-by-point focusing during the process of beam-forming, while saving memory resources.

DETAILED DESCRIPTION

Figure 1:
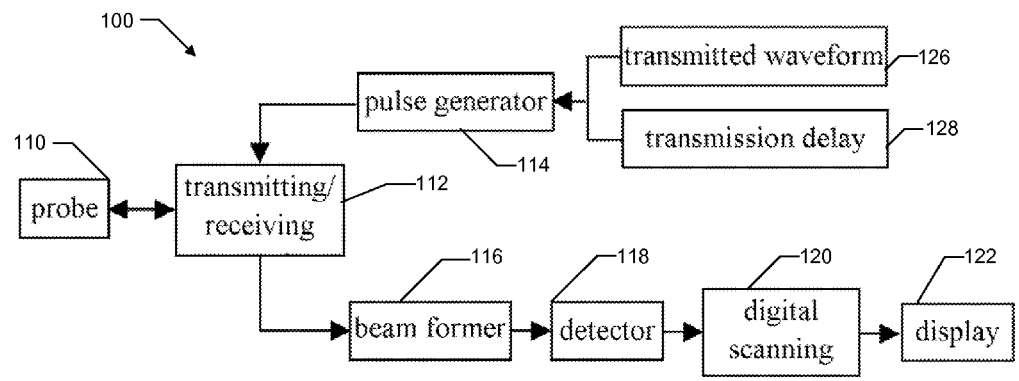
FIG. 1 is a block diagram of an ultrasonic imaging system according to one embodiment.

In an ultrasonic imaging apparatus, an apodization coefficient is an important parameter for beam-forming. A general beam-forming method includes computing and storing the desired apodization coefficients in memory, which are then read for beam-forming. To save memory resources, the apodization coefficients are typically computed for some fixed receiving positions. These fixed receiving positions share the same parameter with the adjacent positions. Therefore, point-by-point apodization is generally not achieved in conventional systems.

Conventional beam-forming systems generally need to maintain one integral apodization coefficient curve for each of a plurality of receiving positions, which consumes a huge amount of memory resources and does not achieve a point-by-point apodization. A method for real-time computation of apodization coefficients of receiving focus points includes pre-storing a group of computed apodization coefficients into memory, and extracting different coefficients from the group of preset curves of the stored apodization coefficients at different receiving depths, so as to obtain apodization curves with different depths. Although this method may store only one apodization coefficient curve, which significantly saves memory resources, it is limited to the amount of apodization coefficients that need to be stored and does not achieve point-by-point apodization.

Thus, the present disclosure provides a method for real-time computation of apodization coefficients and real-time generation of apodization coefficients used during beam-forming with, for example, hardware so as to achieve point-by-point apodization. The disclosed embodiments realize point-by-point focusing during the process of beam-forming, while saving memory resources.

In one embodiment, a method for real-time computation of point-by-point apodization coefficients used for beam-forming includes storing apodization coefficients of receiving focus points into memory, and computing an included angle between a vector from a transducer element to a first receiving point and a normal vector of the transducer element, or computing a trigonometric function value of the included angle. The method also includes using a quantized included angle or a trigonometric function value of the included angle as the target address of the memory, and reading the apodization coefficients. The trigonometric function of the included angle as mentioned above may include a sinusoidal function, a cosine function, a tangent function, or a cotangent function.

In certain embodiments, the method for real-time computation of point-by-point apodization coefficients used for beam-forming also includes, for each of a plurality of receiving channels, computing in advance apodization coefficients of a receiving focus point as the starting point for the subsequent interpolation operation and another receiving focus point as the ending point, and deriving apodization coefficients of the points situated between these two receiving focus points through an interpolation operation. The apodization coefficients may be computed using the following expression:

$$\mathrm{Apod}(j,m) = \mathrm{Apod}(j,i) + \Delta * m/N,$$

in which $\Delta = \mathrm{Apod}(j, i+N) - \mathrm{Apod}(j, i)$, $j$ stands for the serial number of the receiving transducer elements, $m$ is the $i^{th}$ receiving focus point to the $(i+N-1)^{th}$ receiving focus point, and $N$ is the number of the apodization coefficients between the interpolation starting point and the interpolation ending point. The number $N$ of the apodization coefficients between the interpolation starting point and interpolation ending point is selected, in one embodiment, as the power of 2 such that the division by $N$ may be carried out through a shift operation.

In certain embodiments, an absolute value may be taken for the trigonometric function of the included angle and then quantized to become the target address of the memory. Subsequently, the apodization coefficients are read out according to the target address.

In addition, or in other embodiments, when the included angle between the vector from the transducer element to the receiving point and the normal vector of the transducer element, or the absolute value of the trigonometric function thereof, is greater than a predetermined threshold, the apodization coefficients are regarded as zero.

The apodization coefficients may be computed in advance and may be stored in memory in an ascending order.

In the case of a convex transducer array, the included angle $\phi$ or the tangent value thereof may be calculated as follows:

$$\tan(\phi)=(X-K*Y)/(Y+K*X),$$

in which X=Fx−Ex, Y=Fy−Ey, K=tan($\phi$1); Ex, Ey are coordinates of the probe; Fx, Fy are coordinates of the receiving focus point; $\phi$1 is the included angle between the normal vector of the transducer element and the Y axis; and with the probe parameters given, tan($\phi$1) may be determined.

In the case of a linear transducer array and a phased transducer array, the included angle $\phi$ or the tangent value thereof may be calculated as follows:

$$\tan(\phi)=X/Y,$$

in which X=Fx−Ex, Y=Fy−Ey; Ex, Ey are coordinates of the probe; and Fx, Fy are coordinates of the receiving focus point.

In another embodiment, a device for real-time computation of point-by-point apodization coefficients used for beam-forming includes an apodization curve memory for storing apodization coefficients, and a storing unit for storing transducer element coordinates Ex, Ey and K, wherein K=tan($\phi$1), $\phi$1 is the included angle between the normal vector of the receiving transducer element and the Y axis, and tan($\phi$1) may be determined once the probe parameters are given. The device also includes a timer control unit for generating coordinates Fx, Fy of a receiving focus point, and a channel counter for sequentially reading for each receiving channel the corresponding transducer element coordinates Ex, Ey and the tangent value K of the included angle between the normal vector of the transducer element and the Y axis from the storing unit. The device further includes a computation unit for computing an included angle $\phi$ between a vector from a transducer element to a receiving point and a normal vector of the transducer element, or the trigonometric function value thereof on the basis of the transducer element coordinates Ex, Ey, the tangent value K of the included angle between the normal vector of the transducer element and the Y axis, and the receiving focus point coordinates Fx, Fy; and an address processing unit for using a quantized value of the included angle $\phi$ between the vector from the transducer element to the receiving point and the normal vector of the transducer element as the target address of the apodization curve memory, and reading the apodization coefficients Apod(j, i), or taking the absolute value of the trigonometric function value of the included angle $\phi$ between the vector from the transducer element to the receiving point and the normal vector of the transducer element, then using the quantified value thereof as the target address of the apodization curve memory and reading the apodization coefficients Apod(j, i).

In certain embodiments, the trigonometric function of said included angle $\phi$ is tan($\phi$), and the computation unit includes a first subtracter for computing X=Fx−Ex, a second subtracter for computing Y=Fy−Ey; a first multiplier for computing KX, a second multiplier for computing KY, a third subtracter for computing X−KY, a first adder for computing Y+KX, and a divider for computing (X−KY)/(Y+KX).

In addition, or in other embodiments, the device may further include an interpolation unit for using the apodization coefficients of the receiving focus point as the interpolation starting point and the receiving focus point as the interpolation ending point computed for each receiving channel, and deriving through an interpolation procedure apodization coefficients of the points between these two receiving focus points. The number of the interpolation units may the same as that of the receiving channels, and the interpolation unit may perform the interpolation operation according to the following expression:

$$\text{Apod}(j,m)=\text{Apod}(j,i)+\Delta*m/N,$$

in which $\Delta$=Apod(j, i+N)−Apod(j, i), j stands for the serial number of the receiving transducer elements, m is the $i^{th}$ receiving focus point to the $(i+N-1)^{th}$ receiving focus point, and N is the number of the apodization coefficients between two receiving focus points.

In certain embodiments, the interpolation unit includes a first register, a second register, and a third register. The first register is for storing the apodization coefficients read out from the apodization coefficient memory, and for storing the apodization coefficients into the second register under the control of a first data enabling signal. The second register is for storing the apodization coefficients into the third register under the control of a second data enabling signal. The interpolation unit may also include a fourth subtracter for computing $\Delta$=Apod(j, i+N)−Apod(j, i), an accumulator for accumulating the $\Delta$ values computed by the fourth subtracter and outputting the current $\Delta$ value under the control of a reset signal, a shifter for shifting (e.g., rightward) the output of the accumulator by $\log_2$ N bits, and a second adder for adding up the output of the shifter and the apodization coefficients in the third register and outputting the apodization coefficients obtained through interpolation. The number N of the apodization coefficients between the two interpolation points may be selected as the power of 2.

In certain embodiments, the first data enabling signal, second data enabling signal, and the accumulator reset signal are generated by the timer control unit.

With the method and device according to the embodiments disclosed herein, real-time and point-by-point computation of apodization coefficients may be achieved for beam-forming. Additional aspects and advantages will be apparent from the disclosure herein.

FIG. 1 shows a B-mode ultrasonic imaging system 100 that includes a probe 110, a transmitting/receiving component 112, a pulse generator 114, a beam former component 116, a detector component 118, a digital scanning component 120, and a display component 122. The pulse generator 114 receives a transmitted waveform 126 and a transmission delay signal 128 and provides ultrasonic pulses to the transmitting/receiving component 112 for transmission through the probe 110. The probe 110 also provides received ultrasonic pulses (echoes) to the transmitting/receiving unit 112. The received ultrasonic pulses are processed by the beam former component 116, the detector component 118, and the digital scanning component 120 for display on the display component 122.

The following example embodiments are directed to a 64-channel single-beam system. However, it should be understood that the disclosed method and device may be adapted for use in a system having different numbers of channels (e.g., 32, 64, 128, and the like) and multiple beams.

1. Example Method for Real-Time Computation of Point-by-Point Anodization Coefficients.

An apodization coefficient is useful as a criterion for assigning weights to the echo waves received on different channels. Generally, the principle for assigning weights is that the transducer elements closer to the receiving line are assigned greater weight, and that the weight varies with the receiving depth. Based on this principle, the apodization coefficient value may be determined by computing the included angle φ between a vector from the transducer element to the receiving point and the normal vector of the transducer element. The greater the φ value, the smaller the apodization coefficient Apod. Thus, derivation of φ may lead to the apodization coefficients, while φ may be acquired by computing the trigonometric function value of φ and then computing the antitrigonometric function thereof. To simplify the computation, the trigonometric function value of φ (e.g., sinusoidal, cosine, tangent, cotangent functions, etc.) is directly utilized to determine the value of Apod according to the corresponding relationship between φ and its trigonometric function value. In an example embodiment, the tan(φ) value is computed, and then used to derive Apod according to the corresponding relationship of φ and tan(φ). The greater tan (φ), the smaller Apod.

Figure 2:
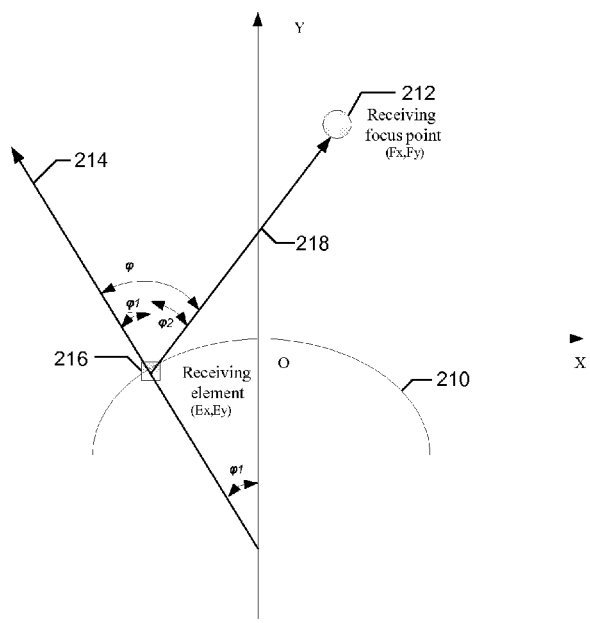
FIG. 2 is a schematic diagram illustrating a computation of an included angle $\phi$ between a vector from a transducer element to a receiving point and a normal vector of the transducer element according to one embodiment.

FIG. 2 shows a method for computing tan(φ) in the case of a convex transducer array (represented by line 210). Because the receiving line may be deviated from the center of the receiving aperture, for generality, the receiving focus point 212 shown lies to the right of the receiving aperture (e.g., at "O" or the intersection of the X axis and the Y axis). φ1 is the included angle between the normal vector 214 of the receiving transducer element 216 (or "receiving element") and the Y axis. tan(φ1) may be determined once the parameters concerning the probe are given. φ2 is the included angle between the vector 218 from the receiving transducer element 216 to the receiving focus point 212 and the Y axis. tan(φ2)=(Fx−Ex)/(Fy−Ey), wherein Ex, Ey denote the known coordinates of the probe, and Fx, Fy are real-time varied coordinates of the receiving focus points 212 during the receiving period. In FIG. 2, the direction of φ1 is defined as the negative direction, and that of φ2 as the positive direction. Therefore, it is derived that:

$$\varphi = \varphi 2 - \varphi 1,$$

$$\text{thus, } \tan(\varphi) = \tan(\varphi 2 - \varphi 1)$$
$$= (\tan(\varphi 2) - \tan(\varphi 1))/(1 + \tan(\varphi 2) * \tan(\varphi 1)).$$

By letting tan(φ1) be K, tan(φ2)=(Fx−Ex)/(Fy−Ey)=X/Y, it follows that $$\tan(\phi)=(X/Y-K)/(1+K*X/Y),$$

and through reorganizing the above equation:

$$\tan(\phi)=(X-K*Y)/(Y+K*X) \qquad (1)$$

wherein X=Fx−Ex, Y=Fy−Ey, K=tan(φ1).

Upon computation of the apodization coefficients for a plurality of points, these apodization coefficients are stored into a memory device in an ascending order. An absolute value is taken for tan(φ) (since φ may be a negative value), which is then quantized and used as the apodization coefficient target address for locating the apodization coefficients.

A greater value for |tan(φ)|, i.e., a greater included angle φ, signifies lower signal energy received by the corresponding receiving transducer element 216. When φ is great enough, i.e., the signal energy received by the corresponding receiving transducer element 216 is low enough, the corresponding transducer element 216 may be deemed as being excluded from the signal-receiving process. Thus, its apodization coefficient is set to zero. In this case, the corresponding value of |tan(φ)| is set as a threshold |tan(ψ)|. For a |tan(φ)| that is greater than |tan(ψ)|, the apodization coefficient thereof is considered to be zero.

Figure 3:
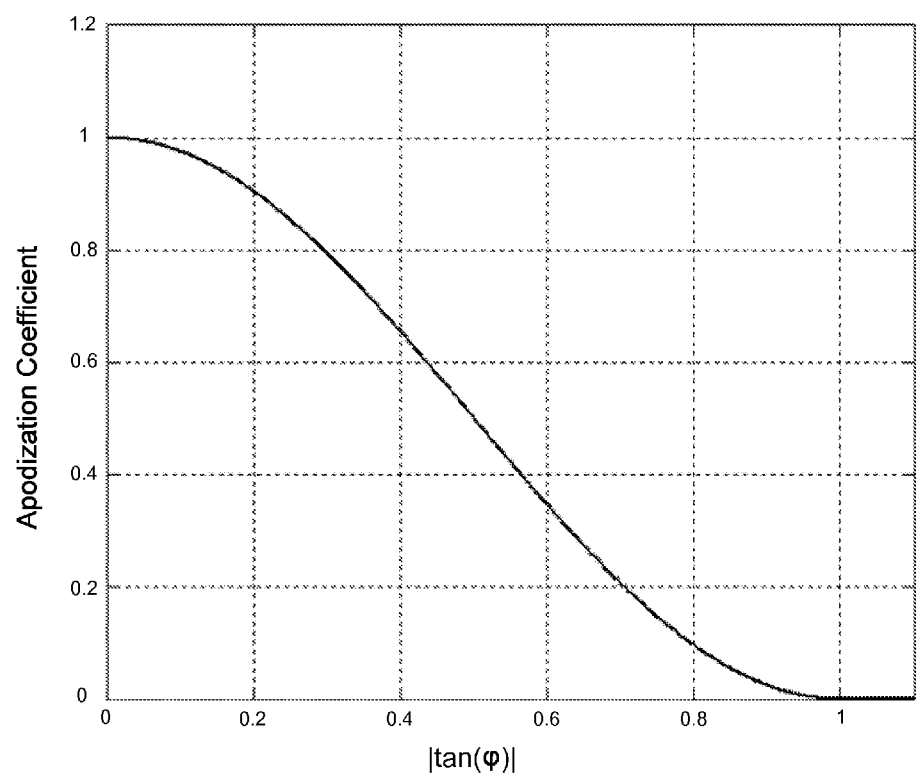
FIG. 3 shows a relationship between $|\tan(\phi)|$ and corresponding apodization coefficients according to one embodiment.
Figure 4:
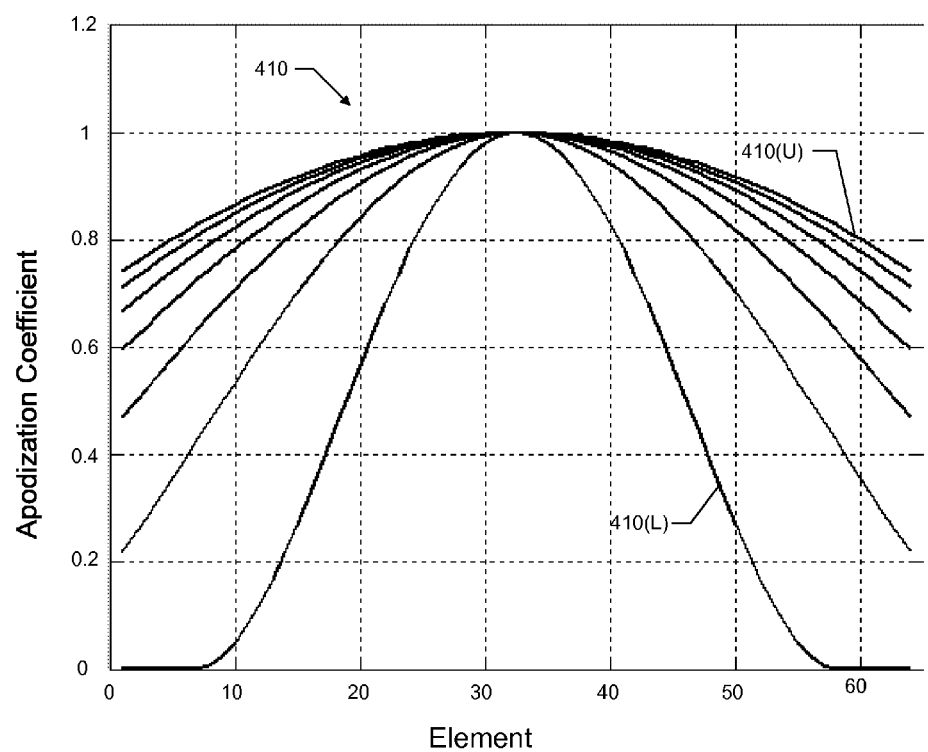
FIG. 4 shows a cluster of apodization coefficient curves with a receiving focus point being situated at the center of a receiving aperture according to one embodiment.

FIG. 3 shows the relationship between |tan(φ)| and corresponding apodization coefficients. The threshold value in FIG. 3 is 1. FIG. 4 shows a cluster of apodization coefficient curves 410 (seven shown) corresponding to respective receiving transducer elements obtained using the above method, wherein the receiving focus points have the following coordinates: (0,11.232), (0,23.552), (0,35.872), (0,48.192), (0,60.512), (0,72.832), (0,85.152) (the units being mm). The horizontal coordinate in FIG. 4 denotes the serial number of the transducer elements, which corresponds to the serial number of the channels. The longitudinal coordinate in FIG. 4 denotes the apodization coefficient value. The receiving focus point with the smallest Y coordinate corresponds to the lowermost curve 410(L), and the receiving focus point with the greatest Y coordinate corresponds to the uppermost curve 410(U).

For a linear transducer array and phased transducer array, the tangent value of the included angle between the receiving focus point and the receiving transducer element is expressed as:

$$\tan(\phi)=(Fx-Ex)/(Fy-Ey)=X/Y \qquad (2),$$

wherein X=Fx−Ex, Y=Fy−Ey.

As one skilled in the art will recognize, equation (2) is included in equation (1) because the normal vector of the transducer element of a linear transducer array or phased transducer array is parallel to the Y axis, and the value of K is constantly zero.

Thus, once the type of the array and its relevant parameters are given, the value of tan(φ) may be computed through equation (1). Thus, the apodization coefficient value may be determined.

As shown in equation (1), the computation of tan(φ) requires the operation of multiplication twice, addition/subtraction twice, and division once. In the case of 64 receiving channels, each channel may use such a computation procedure. Therefore, if this method alone is used for real-time computation of the apodization coefficients of each receiving focus point, a huge amount of computation may be performed. Further, each channel may independently access the memory for reading the apodization coefficient value, leading to a large overhead of hardware resources. Therefore, simpler and more convenient computation methods are discussed below.

For the apodization coefficients corresponding to the same receiving channel, the apodization coefficients for two receiving focus points (i.e., one receiving focus point as an interpolation starting point and the other receiving focus point as an interpolation ending point) may be first computed by equation (1). The remaining N apodization coefficients between these two end points may be obtained through interpolation. In one embodiment, the principle for selecting the number N is that the apodization coefficients of the intermediate position obtained through interpolation based on the apodization coefficients at the two end focusing positions are closest to ideal or desired apodization coefficients. The interpolation algorithm is given in equation (3) as:

$$\text{Apod}(j,m)=\text{Apod}(j,i)+\Delta*m/N \qquad (3),$$

wherein Δ=Apod(j, i+N)−Apod(j, i), j stands for the serial number of the receiving transducer elements, and m is the $i^{th}$ receiving focus point to the $(i+N-1)^{th}$ receiving focus point.

In case N is the power of 2, division by N may be simply replaced by a shift operation, and the Δ*m may be achieved via accumulation. After Apod(j, i+N) and Apod(j, i) are computed by equation (1), each channel asks for only one accumulator, one adder, and one shift operation for real-time computation of the apodization coefficients for each receiving point. As compared with the computation of equation (1), the hardware overhead is significantly reduced.

An advantage for obtaining the apodization coefficients of each receiving focus point through the interpolation operation lies in that the method is not subjected to the influence of "apodization coefficient mutation," which is incurred when a plurality of adjacent receiving points of the same receiving channel share one apodization coefficient.

Figure 5:
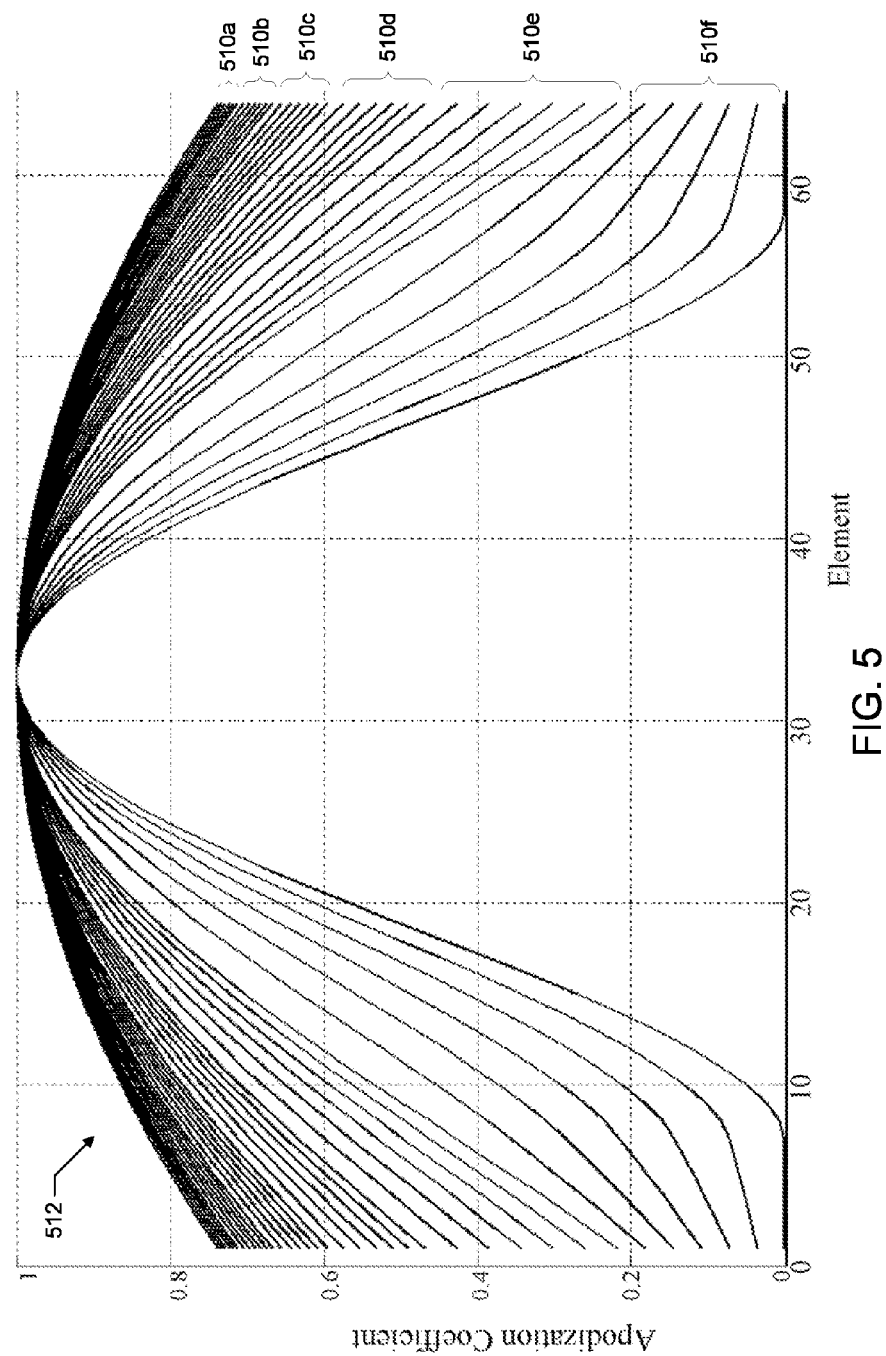
FIG. 5 shows a cluster of apodization coefficient curves obtained through interpolation, with the receiving focus point being situated at the center of the receiving aperture according to one embodiment.

FIG. 5 shows a cluster of six groups 510a-510f (six curves for each group) of apodization coefficient curves 512 obtained through interpolation, taking the seven apodization curves 410 in FIG. 4 as the starting point and the ending point, respectively, where N=6. From FIG. 5, it can be seen that each group 510a-510f of the interpolation-derived apodization coefficient curves 512 is uniformly distributed between a respective starting curve and the ending curve. It may, therefore, be predicted that, when the distance between the starting curve and the ending curve is reduced, and N is increased to a degree that the apodization coefficient of each receiving focus point can be computed in real time, the apodization coefficient curves 512 will have a denser distribution so as to effectively reduce the mutation of the apodization coefficient during the receiving process.

Figure 6:
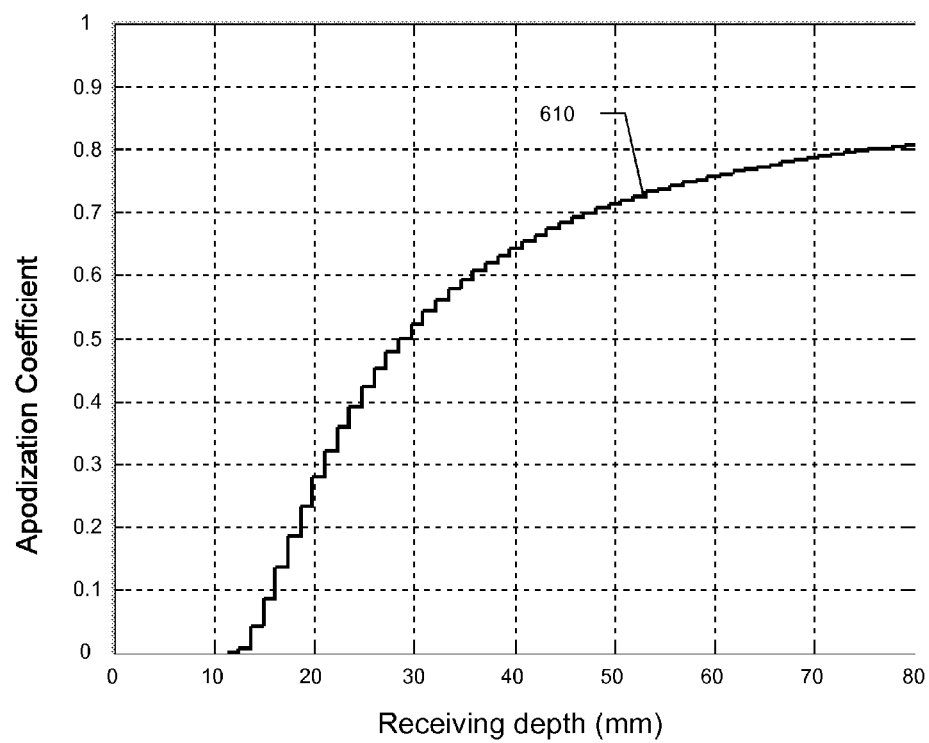
FIG. 6 shows a curve representing the variation of sixth-channel apodization coefficients with different receiving depths before interpolation according to one embodiment.
Figure 7:
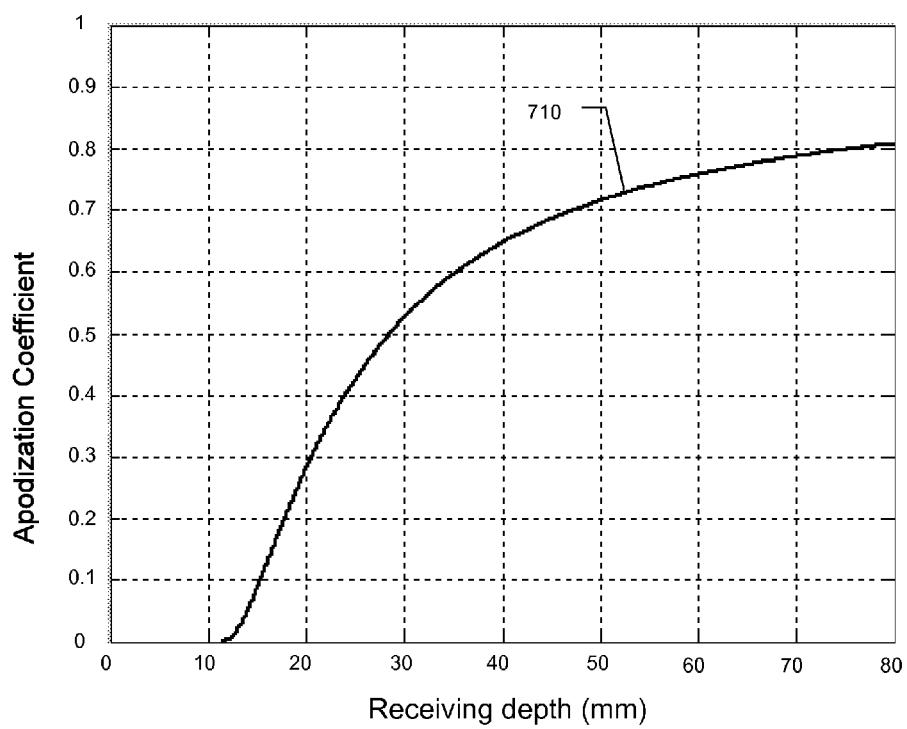
FIG. 7 shows a curve representing the variation of the sixth-channel apodization coefficients with different receiving depths after interpolation according to one embodiment.

Through comparison of the curves representing the variation of the apodization coefficient with the receiving depth before and after interpolation, it can be appreciated more thoroughly how the coefficient variation after interpolation contributes to improving the image quality. FIG. 6 shows a curve 610 representing the variation of sixth-channel apodization coefficients with different receiving depths before interpolation, and FIG. 7 shows a curve 710 representing the variation of the sixth-channel apodization coefficients with different receiving depths after interpolation. A comparison reveals that before interpolation, the apodization curve 610 exhibits an obvious staircase-like variation with different receiving depths, which is particularly obvious when the receiving depth is relatively shallow. In contrast, the curve 710 after interpolation becomes significantly smoother. With the increase of the receiving depth, the apodization coefficient of each receiving point smoothly increments, and the mutation of the coefficient is eliminated. The same conclusion may also be reached in the case of different numbers of channels.

2. Example Device for Real-Time Computation of Point-by-Point Anodization Coefficients.

In the following embodiment, a 64-channel single-beam ultrasonic imaging system is used as an example. In the beamforming process, apodization coefficients are computed for at most 64 channels. However, one skilled in the art will recognize that any number of channels may be used.

Figure 8:
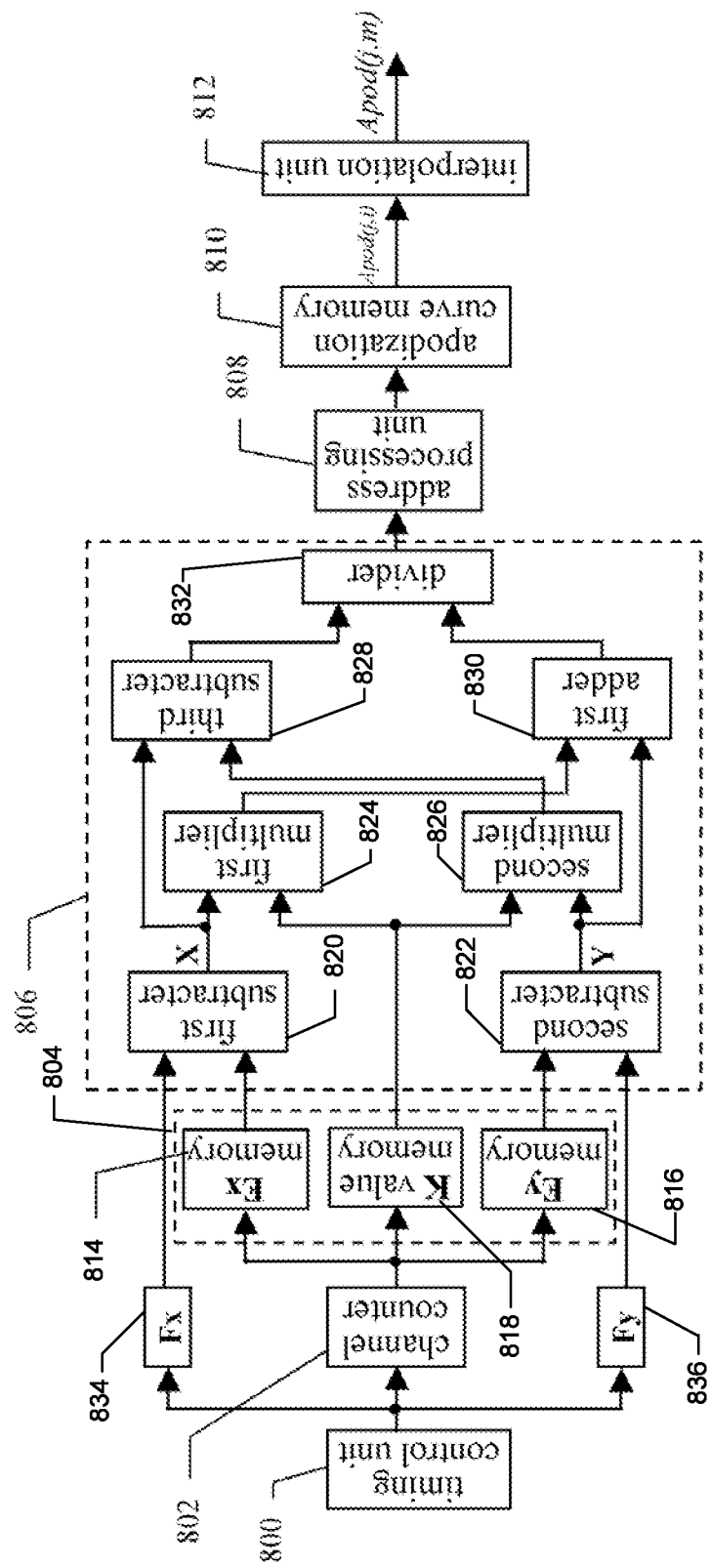
FIG. 8 is a block diagram illustrating a device for real-time computation of point-by-point apodization coefficients according to one embodiment.

As shown in FIG. 8, a device for real-time computation of point-by-point apodization coefficients in accordance with one embodiment includes a timer control unit 800, a channel counter 802, a storing unit 804, a computation unit 806, an address processing unit 808, an apodization curve memory 810, and an interpolation unit 812. In one embodiment, the interpolation unit 812 is optional. If the interpolation unit 812 is provided, the apodization coefficients are computed from the starting point and the ending point of each channel only. Then, the interpolation unit 812 determines the apodization coefficients of the points between the interpolation starting point and the interpolation ending point. If the interpolation unit 812 is not provided, the device in accordance with one embodiment is also capable of computing the apodization coefficients of all points for each channel. In the example embodiment shown in FIG. 8, the interpolation unit 812 is provided. The respective units of the device according to such an embodiment are explained in detail below.

The storing unit 804 includes a transducer element coordinate Ex memory 814 and Ey memory 816, and K value memory 818. The computation unit 806 includes a first subtracter 820, a second subtracter 822, a first multiplier 824, a second multiplier 826, a third subtracter 828, a first adder 830, and a divider 832. Of course, as one skilled in the art will recognize, the computation unit 806 may have a different configuration configured perform the computation of equation (1).

The timer control unit 800 controls in a manner to generate the Fx value 834 and the Fy value 836. The channel counter 802 starts to count and read out in sequence corresponding transducer element coordinates Ex, Ey of each receiving channel and the tangent value K of the transducer element normal vector (for a linear transducer array and phased transducer array, the K value is 0) from the respective memories 814, 816, 818 in the storing unit 804. The first subtracter 820 computes the value of X (i.e., X=Fx−Ex), the second subtracter 822 computes the value of Y (i.e., Y=Fy−Ey), the first multiplier 824 computes KX, the second multiplier 826 computes KY, the third subtracter 828 computes (X−KY), the first adder 830 computes (Y+KX), and the divider 832 computes (X−KY)/(Y+KX) (i.e., $\tan(\phi)$=(X−KY)/(Y+KX)). Having taken an absolute value of the computed $\tan(\phi)$, the address processing unit 808 processes $|\tan(\phi)|$ according to the preset threshold value $|\tan(\psi)|$. If $|\tan(\phi)|>|\tan(\psi)|$, $|\tan(\psi)|$ is outputted. The quantized $|\tan(\phi)|$ is adopted as the target address of the apodization curve memory 810, and then the apodization coefficient value Apod(j, i) is read out and outputted.

Before the receiving process starts, the apodization coefficients are first computed for two receiving focus points Apod (j,0), Apod(j,N), (0≤j<64) of each of the 64 channels. These apodization coefficients of the corresponding two receiving points for each channel are inputted into the interpolation unit 812. The number of the interpolation units 812 corresponds to the number of the channels. For example, 64 channels uses 64 interpolation units.

Figure 9:
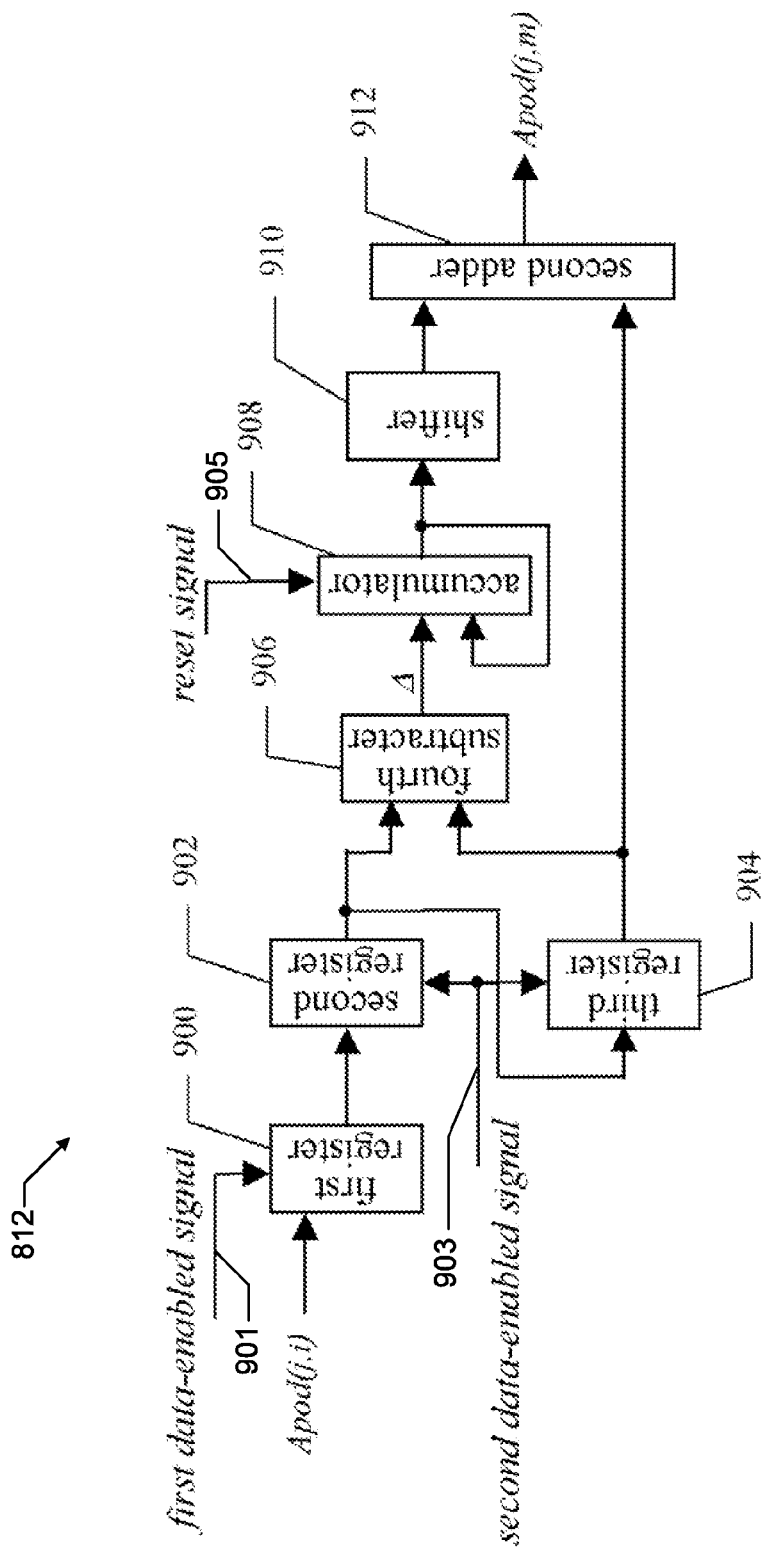
FIG. 9 is a block diagram illustrating an interpolation unit of the device shown in FIG. 8 for real-time computation of point-by-point apodization coefficients according to one embodiment.

FIG. 9 shows the structure of the interpolation unit 812 in accordance with one embodiment for performing the computation of equation (3). Under the control of a first data enabling signal 901 (e.g., this signal 901 may be generated by the above-mentioned timer control unit 800, one for each interpolation unit 812), the apodization coefficient Apod(j, i) is first inputted into a corresponding first register 900 of channel j in the interpolation unit 812. When Apod(0, i) to Apod(63, i) are computed and stored in the first registers 900 in each of the 64 interpolation units, the timer control unit 800 generates a second data enabling signal 903 to store Apod(j, i) in a second register 902. Apod(j, i+N) is read out continuously, and stored under the control of the first data enabling signal 901 in the first register 900 of each channel interpolation unit 812. When Apod(0, i+N) to Apod(63, i+N) are stored in the first registers 900 of each of the 64 interpolation units 812, the timer control unit 800 again generates the second data enabling signal 903 to store Apod(j, i+N) in the second register 902, and synchronously store Apod(j, i) in a third register 904. Apod(j, i+2*N) continues to be read out and stored in the first register 900 of each channel interpolation unit 812 to be updated.

After the contents of both the second register 902 and the third register 904 are updated, the timer control unit 800 generates an accumulator reset signal 905 to reset the output of an accumulator 908 to the current Δ value. A fourth subtracter 906 computes Δ=Apod(j, i+N)−Apod(j, i). The accumulator 908 accumulates the Δ values computed by the fourth subtracter 906.

When the receiving process begins, i is equal to 0. When receiving from 0 to $(N-1)^{th}$ receiving points, the interpolation unit 812 computes 0 to $(N-1)^{th}$ apodization coefficients based on the inputted Apod(j,0) and Apod(j,N). When it comes to receiving point N, Apod(j,N) is stored in the third register 904 and Apod(j,2*N) is stored in the second register 902. Therefore, the apodization coefficients of the points N to 2*N−1 may be derived based on Apod(j,N) and Apod(j,2*N) through interpolation.

During the receiving process, assuming that the apodization coefficient stored in the third register 904 is Apod(j, i), the apodization coefficient stored in the second register 902 is Apod(j, i+N). The apodization coefficients Apod(j, i+2*N) are successively read out in advance based on the computed |tan(φ)| and are stored in the first registers 900 of each channel interpolation unit 812 in order. After the computation of the apodization coefficients of N receiving points is completed, the timer control unit 800 generates the second data enabling signal 903, enabling the apodization coefficient in the second register 902 to be stored in the third register 904, and the apodization coefficient in the first register 900 to be stored in the second register 902. Subsequently, the accumulator reset signal 905 is generated to reset the output of the accumulator 908 to the updated Δ value. The above steps are repeated until the apodization coefficients of each receiving focus point are determined.

To save resources, the number N of the points between two interpolation points according to one embodiment is selected to be the power of 2. In this way, the division in equation (3) may be replaced by a shift operation. That is, a shifter 910 shifts (e.g., to the right) the output of the accumulator 908 by $\log_2 N$ bits to complete the division operation in equation (3). In computing of Δ*m, because Δ is a constant value between 0 and the $(N-1)^{th}$ point, a single accumulator 908 may be used in place of a multiplication circuit. The second adder 912 adds up the output of the shifter 910 and the apodization coefficients in the third register 904, and outputs the apodization coefficients obtained through interpolation.

The method and device according to the disclosed embodiments have been described using a 64-channel single-beam system as an example. However, the present disclosure is not limited to these particular embodiments. One skilled in the art will recognize that the disclosed method and device may also be applied to other systems. For example, in the case of different numbers of channels, it may only be necessary to change the number of the interpolation circuits to adapt to different numbers of channels. When multiple beams are used, each beam may uses one complete set of circuitry described above. Therefore, any modification or substitution made to the disclosed embodiments should be regarded as being within the scope of the present invention.

A person of ordinary skill in the art will recognize that the described features, operations, or characteristics disclosed herein may be combined in any suitable manner in one or more embodiments. It will also be readily understood that the order of the steps or actions of the methods described in connection with the embodiments disclosed may be changed as would be apparent to those skilled in the art. Thus, any order in the drawings or Detailed Description is for illustrative purposes only and is not meant to imply a required order, unless specified to require an order.

Embodiments may include various steps, which may be embodied in machine-executable instructions to be executed by a general-purpose or special-purpose computer (or other electronic device). Alternatively, the steps may be performed by hardware components that include specific logic for performing the steps or by a combination of hardware, software, and/or firmware.

Embodiments may also be provided as a computer program product including a machine-readable medium having stored thereon instructions that may be used to program a computer (or other electronic device) to perform processes described herein. The machine-readable medium may include, but is not limited to, hard drives, floppy diskettes, optical disks, CD-ROMs, DVD-ROMs, ROMs, RAMs, EPROMs, EEPROMs, magnetic or optical cards, solid-state memory devices, or other types of media/machine-readable medium suitable for storing electronic instructions.

As used herein, a software module or component may include any type of computer instruction or computer executable code located within a memory device and/or transmitted as electronic signals over a system bus or wired or wireless network. A software module may, for instance, comprise one or more physical or logical blocks of computer instructions, which may be organized as a routine, program, object, component, data structure, etc., that performs one or more tasks or implements particular abstract data types.

In certain embodiments, a particular software module may comprise disparate instructions stored in different locations of a memory device, which together implement the described functionality of the module. Indeed, a module may comprise a single instruction or many instructions, and may be distributed over several different code segments, among different programs, and across several memory devices. Some embodiments may be practiced in a distributed computing environment where tasks are performed by a remote processing device linked through a communications network. In a distributed computing environment, software modules may be located in local and/or remote memory storage devices. In addition, data being tied or rendered together in a database record may be resident in the same memory device, or across several memory devices, and may be linked together in fields of a record in a database across a network.

It will be understood by those having skill in the art that many changes may be made to the details of the above-described embodiments without departing from the underlying principles of the invention. The scope of the present invention should, therefore, be determined only by the following claims.

What is claimed is:

1. A method for real-time computation of point-by-point apodization coefficients used for beam-forming during ultrasound imaging, comprising:
    obtaining ultrasonic pulses by transmitting and receiving via a probe;
    assigning weights to received echo waves to compute an apodization coefficient on each different channel by a computer;
    storing apodization coefficients of receiving focus points in a memory;
    computing at least one of an included angle formed by a vector from a transducer element to a first receiving focus point and a normal vector of the transducer element, and a trigonometric function value of the included angle using the computer; and
    reading the apodization coefficients by using at least one of a quantization of the included angle, and the trigonometric function value as a target memory address to access a location in the memory indexed by the target memory address;

for each of a plurality of receiving channels, computing apodization coefficients of a second receiving focus point as a starting point for a subsequent interpolation operation and a third receiving focus point as an ending point for the interpolation operation; and deriving apodization coefficients of the points situated between the second receiving focus point and the third receiving focus point through the interpolation operation;

wherein an apodization coefficient Apod is computed using the following expression:

$$Apod(j,m)=Apod(j,i)+\Delta *m/N,$$

in which, $\Delta$=Apod(j, i+N)−Apod(j, i), j stands for a serial number of the receiving transducer elements, m is the $i^{th}$ receiving focus point to the $(i+N-1)^{th}$ receiving focus point, and N is the number of the apodization coefficients between the interpolation starting point and the interpolation ending point.

2. The method of claim 1, wherein the number N of the apodization coefficients between the interpolation starting point and the interpolation ending point is selected as a power of 2 such that the division by N is realized through a shift operation.

3. The method of claim 1, further comprising:
computing an absolute value for the trigonometric function value of the included angle; and
quantizing the absolute value to become the target address of the memory via which the apodization coefficients are read out.

4. The method of claim 1, wherein if at least one of the included angle and the absolute trigonometric function value thereof is greater than a predetermined threshold, the apodization coefficients are regarded as zero.

5. The method of claim 1, wherein the trigonometric function of the included angle is selected from a group comprising a sinusoidal function, a cosine function, a tangent function, and a cotangent function.

6. The method of claim 1, wherein the apodization coefficients are computed and are stored in the memory in ascending order.

7. The method of claim 1, wherein the transducer element is included in a convex transducer array, the method further comprising calculating the included angle $\phi$ or the tangent value thereof as follows:

$$\tan(\phi)=(X-K*Y)/(Y+K*X);$$

in which X=Fx−Ex, Y=Fy−Ey, K=tan($\phi$1), Ex, Ey are coordinates of the transducer array, Fx, Fy are coordinates of the first receiving focus point, $\phi$1 is an included angle between the normal vector of the transducer element and the Y axis, and tan($\phi$1) is based on transducer array parameters.

8. The method of claim 1, wherein the transducer element is included in one of a linear transducer array and a phased transducer array, the method further comprising calculating at least one of the included angle $\phi$ and the tangent value thereof as follows:

$$\tan(\phi)=X/Y,$$

in which X=Fx−Ex, Y=Fy−Ey; Ex, Ey are coordinates of the transducer array, and Fx, Fy are coordinates of the first receiving focus point.

9. A device for real-time computation of point-by-point apodization coefficients used for beam-forming, comprising:
an ultrasonic probe for transmitting and receiving ultrasonic pulses;
a computer comprising:
an apodization curve memory to store apodization coefficients;
a storing unit to store transducer element coordinates Ex, Ey and K, wherein K=tan($\phi$1), $\phi$1 is an included angle between a normal vector of a transducer element and the Y axis, and tan($\phi$1) is determined based on probe parameters;
a timer control unit to generate coordinates Fx, Fy of a receiving focus point;
a channel counter to sequentially read out, for each of a plurality of receiving channels, the corresponding transducer element coordinates Ex, Ey and the tangent value K of the included angle between the normal vector of the transducer element and the Y axis;
wherein the computer is to compute at least one of an included angle $\phi$ formed by a vector from a first transducer element to a receiving point and a normal vector of the transducer element, and a trigonometric function value thereof based on the transducer element coordinates Ex, Ey, the tangent value K of the included angle between the normal vector of the transducer element and the Y axis, and the receiving focus point coordinates Fx, Fy; and
an address processing unit to at least one of:
use a quantized value of the included angle $\phi$ formed by the vector from the transducer element to the first receiving point and the normal vector of the transducer element as a target memory address to access a location in the apodization curve memory indexed by the target memory address, and read out the apodization coefficients Apod(j, i); and
take the absolute value of trigonometric function value of the included angle $\phi$ between the vector from the transducer element to the receiving point and the normal vector of the transducer element, use the quantified value thereof as the target address of the apodization curve memory, and read out the apodization coefficients Apod(j, i);
an interpolation unit to:
use the apodization coefficient of a second receiving focus point as an interpolation starting point and the apodization coefficient of a third receiving focus point as an interpolation ending point for each receiving channel; and
derive through an interpolation procedure apodization coefficients of the points between the second receiving focus point and the third receiving focus point;
wherein the interpolation unit performs the interpolation operation based on the following expression:

$$Apod(j,m)=Apod(j,i)+\Delta *m/N;$$

in which, $\Delta$=Apod(j, i+N)−Apod(j, i), j stands for the serial number of the receiving transducer elements, m is the $i^{th}$ receiving focus point to the $(i+N-1)^{th}$ receiving focus point, and N is the number of the apodization coefficients between second receiving focus point and the third receiving focus point.

10. The device of claim 9, wherein the trigonometric function of the included angle $\phi$ is tan($\phi$).

11. The device of claim 10, wherein the computation unit comprises:
a first subtracter to compute X=Fx−Ex;
a second subtracter to compute Y=Fy−Ey;
a first multiplier to compute KX;
a second multiplier to compute KY;
a third subtracter to compute X−KY;
a first adder to compute Y+KX; and a divider to compute (X−KY)/(Y+KX).

12. The device of claim 9, wherein the interpolation unit comprises:
> a first register, a second register, and a third register, the first register to store the apodization coefficients read out from the apodization coefficient memory, and store the apodization coefficients into the second register under the control of a first data enabling signal, the second register to store the apodization coefficients into the third register under the control of a second data enabling signal;
> a fourth subtracter to compute $\Delta = \text{Apod}(j, i+N) - \text{Apod}(j, i)$;
> an accumulator to accumulate the $\Delta$ values computed by the fourth subtracter and output the current $\Delta$ value under the control of a reset signal;
> a shifter to shift the output of the accumulator by $\log_2 N$ bits; and
> a second adder to add up the output of the shifter and the apodization coefficients in the third register, and output the apodization coefficients obtained through interpolation,
> wherein the number N of the apodization coefficients between the interpolation starting point and the interpolation ending point is selected as the power of 2.

13. The device of claim 12, wherein the first data enabling signal, the second data enabling signal, and the accumulator reset signal are generated by the timer control unit.

14. The device of claim 9, wherein the number of interpolation units is the same as that of the receiving channels.

15. A non-transitory computer-readable storage medium comprising program code for performing a method for real-time computation of point-by-point apodization coefficients used for beam-forming during ultrasound imaging, the method comprising:
> obtaining ultrasonic pulses by transmitting and receiving via a probe;
> assigning weights to received echo waves to compute an apodization coefficient on each different channel by a computer;
> storing apodization coefficients of receiving focus points in a memory;
> computing at least one of an included angle formed by a vector from a transducer element to a first receiving focus point and a normal vector of the transducer element, and a trigonometric function value of the included angle; and
> reading the apodization coefficients by using at least one of a quantization of the included angle, and the trigonometric function value as a target memory address to access a location in the memory indexed by the target memory address;
> for each of a plurality of receiving channels, computing apodization coefficients of a second receiving focus point as a starting point for a subsequent interpolation operation and a third receiving focus point as an ending point for the interpolation operation; and
> deriving apodization coefficients of the points situated between the second receiving focus point and the third receiving focus point through the interpolation operation;
> wherein an apodization coefficient Apod is computed using the following expression:
>
> $$\text{Apod}(j,m) = \text{Apod}(j,i) + \Delta * m/N,$$
>
> in which, $\Delta = \text{Apod}(j, i+N) - \text{Apod}(j, i)$, i stands for a serial number of the receiving transducer elements, m is the $i^{th}$ receiving focus point to the $(i+N-1)^{th}$ receiving focus point, and N is the number of the apodization coefficients between the interpolation starting point and the interpolation ending point.

16. The computer-readable medium of claim 15, wherein the number N of the apodization coefficients between the interpolation starting point and the interpolation ending point is selected as a power of 2 such that the division by N is realized through a shift operation.

17. The computer-readable medium of claim 15, wherein the transducer element is included in a convex transducer array, the method further comprising calculating the included angle $\phi$ or the tangent value thereof as follows:

$$\tan(\phi) = (X - K*Y)/(Y + K*X);$$

in which $X = F_x - E_x$, $Y = F_y - E_y$, $K = \tan(\phi 1)$, Ex, Ey are coordinates of the transducer array, Fx, Fy are coordinates of the first receiving focus point, $\phi 1$ is an included angle between the normal vector of the transducer element and the Y axis, and $\tan(\phi 1)$ is based on transducer array parameters.

18. The computer-readable medium of claim 15, wherein the transducer element is included in one of a linear transducer array and a phased transducer array, the method further comprising calculating at least one of the included angle $\phi$ and the tangent value thereof as follows:

$$\tan(\phi) = X/Y,$$

in which $X = F_x - E_x$, $Y = F_y - E_y$; Ex, Ey are coordinates of the transducer array, and Fx, Fy are coordinates of the first receiving focus point.

* * * * *